United States Patent [19]

Berner

[11] Patent Number: 5,519,210
[45] Date of Patent: May 21, 1996

[54] APPARATUS AND A PROCESS FOR RECORDING PHOTOMETRIC DATA THAT IS POSITIONED IN SUCCESSION OR IN ADJACENT FASHION ON A PAGE-LIKE OR STRIP-LIKE PRINT

[75] Inventor: Markus Berner, Niederhasli, Switzerland

[73] Assignee: Gretag Aktiengesellschaft, Regensdorf, Switzerland

[21] Appl. No.: 234,381

[22] Filed: Apr. 28, 1994

[30] Foreign Application Priority Data

May 13, 1993 [CH]  Switzerland .............................. 1466/93

[51] Int. Cl.[6] ......................................................... G01J 3/51
[52] U.S. Cl. ........................ 250/226; 250/559.01; 356/406
[58] Field of Search ................................. 250/226, 559.1, 250/559.46, 559.01; 356/406, 407, 402, 419, 418, 416, 425, 429, 73, 446; 101/183, 181, 409, 410, 411, 412; 364/526, 525

[56] References Cited

U.S. PATENT DOCUMENTS

| | | | |
|---|---|---|---|
| 4,277,138 | 7/1981 | Dammann | 359/569 |
| 4,645,350 | 2/1987 | Weidmann et al. | 356/418 |
| 4,788,116 | 11/1988 | Hochberg | 430/21 |
| 4,898,467 | 2/1990 | Milch | 356/328 |
| 5,062,714 | 11/1991 | Peterson et al. | 356/406 |
| 5,095,818 | 3/1992 | Bialek | 101/183 |
| 5,118,183 | 6/1992 | Cargill et al. | 356/73 |
| 5,272,518 | 12/1993 | Vincent | 356/405 |

FOREIGN PATENT DOCUMENTS

3930782  1/1991  Germany .

*Primary Examiner*—Edward P. Westin
*Assistant Examiner*—John R. Lee
*Attorney, Agent, or Firm*—Burns, Doane, Swecker & Mathis

[57] ABSTRACT

An apparatus for recording photometric data that is positioned in succession or in adjacent fashion on a page-like or strip-like print is equipped with at least one reflectance measuring unit with a reflectance measuring lens for measuring opaque prints (for example, paper test strips for examining the paper developing baths or for control of the basic printer setting). Wavelength dispersion elements positioned in the light path of the reflected light permit the analysis of the measuring fields according to wavelengths and preferably in the three primary colors of red, green, and blue. The apparatus can be equipped with an automatic transport device for the page-like or strip-like prints; the transport device is positioned behind the measuring lens. The prints are inserted into the device through an intake slot which is designed to accommodate prints of different width. On at least one side of the intake slot there is at least one stop for the prints. Each stop is stationary relative to the intake slot for the prints. The reflectance measuring lens and the print seized by the transport device and transported in the longitudinal direction can be moved in the transverse direction, relative to one other. In this manner it is possible to measure adjacent measuring fields without having to reposition the print between individual measurements.

36 Claims, 6 Drawing Sheets

APPARATUS AND A PROCESS FOR RECORDING PHOTOMETRIC DATA THAT IS POSITIONED IN SUCCESSION OR IN ADJACENT FASHION ON A PAGE-LIKE OR STRIP-LIKE PRINT

BACKGROUND OF INVENTION

The invention relates to an apparatus and a process for recording photometric data that is positioned side by side or in succession on a page-like or strip-like print.

Apparatuses for recording photometric data, so-called densitometers, are variously employed in the photographic industry and in graphics, particularly in printing shops. Basically, densitometers can be employed in all areas that work with preset printings or with test printings. In addition to the mentioned areas of application, densitometers can play a role in desk-top publishing.

In the photographic industry, densitometers are used both in the routine control of apparatus parts involving wet chemistry and in inspecting the adjustment of the photographic copier or photographic printer. In inspecting apparatus parts involving wet chemistry, i.e., the developing baths for film or paper, corresponding chemical strips of film or paper are subjected to measurement. These strips have already been exposed in a standardized fashion by the film or paper manufacturer and are developed over regular distances in the given film or paper developing baths. The developed film or paper strips are photometrically evaluated with the densitometers and are compared with the manufacturer's theoretical specifications. Depending on the results thus ascertained, the developing baths are freshened or supplemented, renewed, or left unchanged. To inspect the adjustment of the photographic printer, one or several standard negatives are exposed on photographic paper and are developed with a tested chemical process. The developed images are photometrically evaluated with the densitometer and compared with the theoretical values. The basic setting of the photographic printer may be modified according to the values ascertained.

This general type of apparatus for recording photometric data on film or paper strips is described in U.S. Pat. No. 5,118,183. The densitometer apparatus is equipped both for reflectance operation with opaque test strips and for transmission operation with transparent test strips and accordingly exhibits a stationary reflectance measuring lens and a stationary transmission measuring lens. Stationary filters in the apparatus also permit the reflectance and transmission densities of the test strip to be determined for different wavelengths, chiefly for the three primary colors of red, green, and blue. A motorized transport device incorporated in the apparatus moves the test strip along the apparatus. A lateral guide element permits improved positioning of the test strip, which is fed into the apparatus through an intake slot. The lateral guide unit can be manually adjusted to the specific width of the test strip. To also permit the evaluation of test strips that have more than one column of test fields—which, for example, can be brought side by side on the test strip in the longitudinal direction—not only can the lateral guide unit be adjusted in its width, it can also be moved in its entirety in a direction transverse to the intake direction of the test strip into the apparatus. This makes it possible to measure several adjacently positioned columns of measuring fields, given some skill and patience.

The film and paper test strips of different manufacturers generally exhibit differently positioned measuring fields. The measuring fields differ in size and, particularly in the case of paper strips, may be positioned side by side in one or several columns. The positioning of successive measuring fields relative to a central track of a column may differ, that is, individual measuring fields may be slightly displaced relative to this central track. Neighboring measuring field columns may also exhibit a different number of measuring fields. The first measuring field of a column may not necessarily be positioned at the same distance from the front edge of the test strip as the first measuring field of the neighboring column. The test strips of different manufacturers thus differ considerably in design. An operator who wishes to measure a test strip with the known apparatus must orient the strip with a great degree of care to assure that the measurement is made at the correct point. Apart from the fact that this orientation process is time-consuming, it is difficult to record measuring fields which may have a displaced position relative to the central track of a column. Here the operator must first visually assess the test strip and then decide which section of the test strip must be fed in displaced fashion relative to the central track of the column, in order to measure both centrally positioned and displaced measuring fields. This is frequently difficult to master, and an erroneous feed of the test strip may result in incorrect measurements and the need to repeat the process. With certain test strips it may even be the case that lateral displacement is insufficient to reach all the measuring fields of a column.

In a known apparatus, a test strip is automatically transported through the apparatus. A pair of rollers, one of which is driven, seizes the advancing end of the test strip and pulls it through. Once the test strip has been seized by the roller pair, it can no longer be displaced laterally. If the test strip exhibits more than one column of measuring fields for measurement, it is consequently necessary to completely measure one column first, and the test strip must transported completely through the apparatus. The test strip is then fed into the apparatus in a laterally displaced position, in such a way that the measuring fields of the adjacent column can be evaluated, etc. Thus, the test strip must be separately oriented for each measuring column, and each time the operator must decide anew which portion of the test strip must be laterally displaced to assure that all measuring fields are reliably covered.

SUMMARY OF INVENTION

A goal of the present invention, therefore, is to remedy these disadvantages of known apparatuses. In particular, it would be desirable to provide an apparatus for recording photometric data that is positioned in succession or in adjacent fashion on a page-like or strip-like print in such a way that the effort involved in correctly positioning the test strip is considerably reduced. The operator should no longer have to decide whether, and to what degree, a test strip is fed in a laterally displaced fashion. The apparatus should permit adjacent measuring columns to be measured without the test strip being oriented anew for each column of measuring fields. It should be possible to measure adjacent measuring fields even when the test strip has been seized by the transport device within the apparatus. The apparatus should be such that test strips of differing width and/or length and with a differing placement of the measuring fields can be measured without error.

In accordance with the exemplary embodiments of the present invention, these problems and other problems related to them are solved by an apparatus and a process for recording photometric data that is positioned side by side or in succession on a page-like or strip-like print. Exemplary embodiments relate to a method and apparatus for recording photometric data by feeding a page-like or strip-like print with measuring fields that are positioned in succession or in adjacent fashion through an intake slot that includes, on at least one side, at least one stop for the prints wherein each stop is stationary relative to the intake slot; automatically drawing via a transport device positioned within a housing, the print along a transport path into the housing and conducting it past a measuring unit which is positioned relative to the intake direction of the print, in front of the transport device within the housing and which is connected to an evaluation unit; measuring the prints by the measuring unit and analyzing the print, in at least three primary colors by means of a wavelength dispersion unit; transmitting recorded data to an electronic evaluation unit for further processing; and moving at least a portion of the measuring unit and the print relative to each other in a direction transverse to the intake direction of the print and toward adjacently positioned measuring fields on the print.

Further, exemplary embodiments are directed to an apparatus for recording photometric data positioned side by side or in succession on a page-like or strip-like print whose design permits it to be built into a photographic printer, but which can also take the form of a "stand-alone" apparatus. Outfitting the apparatus with at least a reflectance measuring lens permits the measurement of opaque prints (for example, paper strips for inspecting paper developing baths or for controlling the basic printer setting). Filters positioned in the path of the measuring light permit the measuring fields to be analyzed in terms of wavelengths, such as the three basic colors of red, green, and blue. The apparatus can be equipped with an automatic transport device for page-like or strip-like prints which is positioned behind the measuring lens in the direction of transport. An intake slot allows the prints to be inserted into the apparatus and can be designed to accommodate differing widths. On at least one side of the intake slot there can be at least one stop for the prints. Each stop is stationary relative to the intake slot for the prints. The reflectance measuring lens and the prints seized by the transport device and moved in the longitudinal direction can be moved relative to one another in a direction transverse to the intake direction. This permits adjacent columns of measuring fields to be measured, without having to reposition the print between individual measurements. The expense in terms of operator manipulation is considerably reduced. The operator need no longer decide whether—and the degree to which—a print (test strip) must be inserted in laterally displaced fashion in assuring that all the measuring fields of adjacent columns can be measured. The operator only has to assure that the print rests against the appropriate stop and that it is fed far enough into the intake slot for it to be seized by the transport device; everything else can be automatically taken care of by the apparatus.

BRIEF DESCRIPTION OF THE DRAWINGS

Other objects and advantages will become apparent from the following detailed description of preferred embodiments of the invention as described in conjunction with the accompanying drawings wherein like reference numerals are applied to like elements and wherein.

DETAILED DESCRIPTION OF THE PREFERRED EMBODIMENTS

Figure 1:
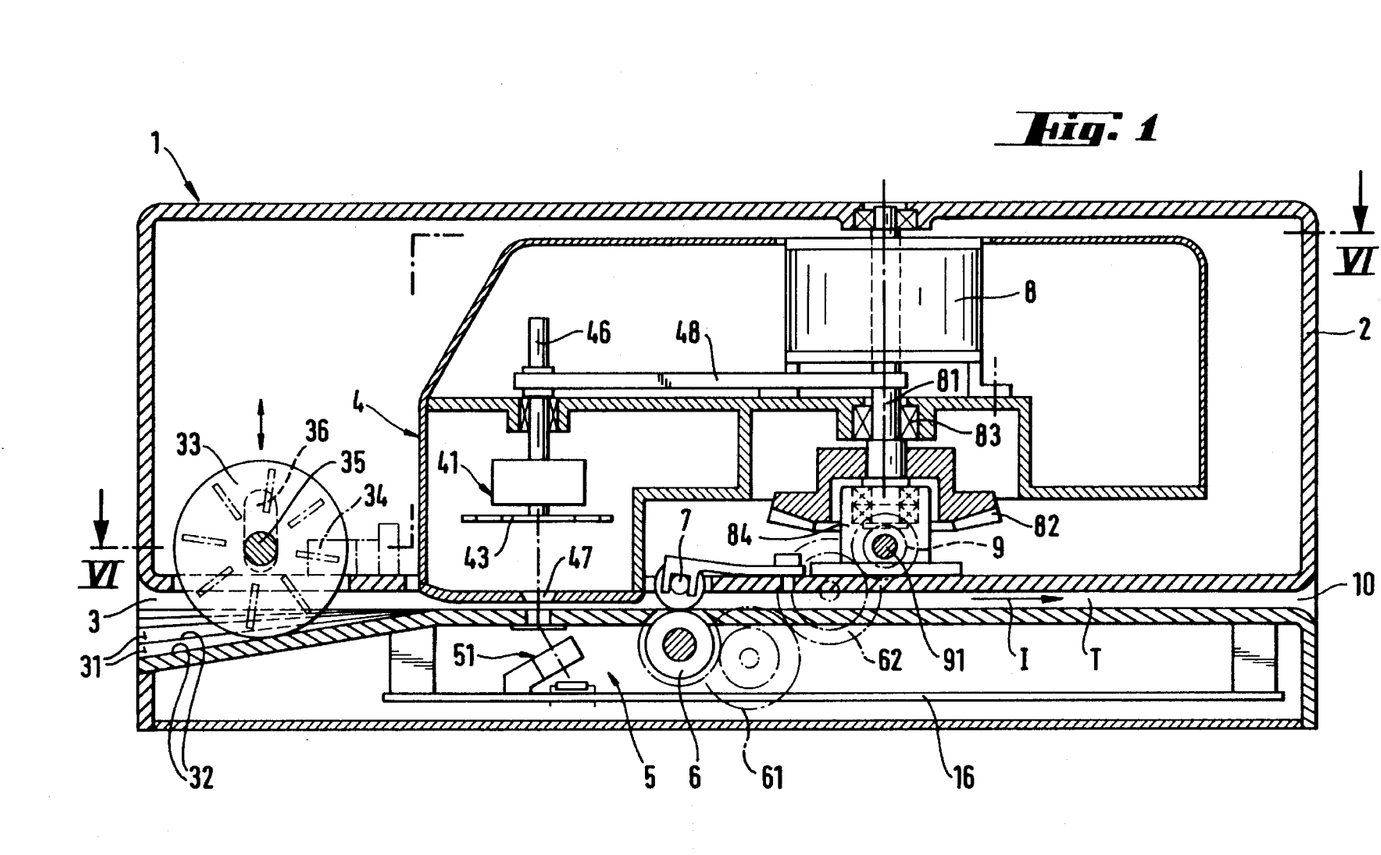
FIG. 1 shows a longitudinal section through an exemplary apparatus according to the invention.
Figure 4:
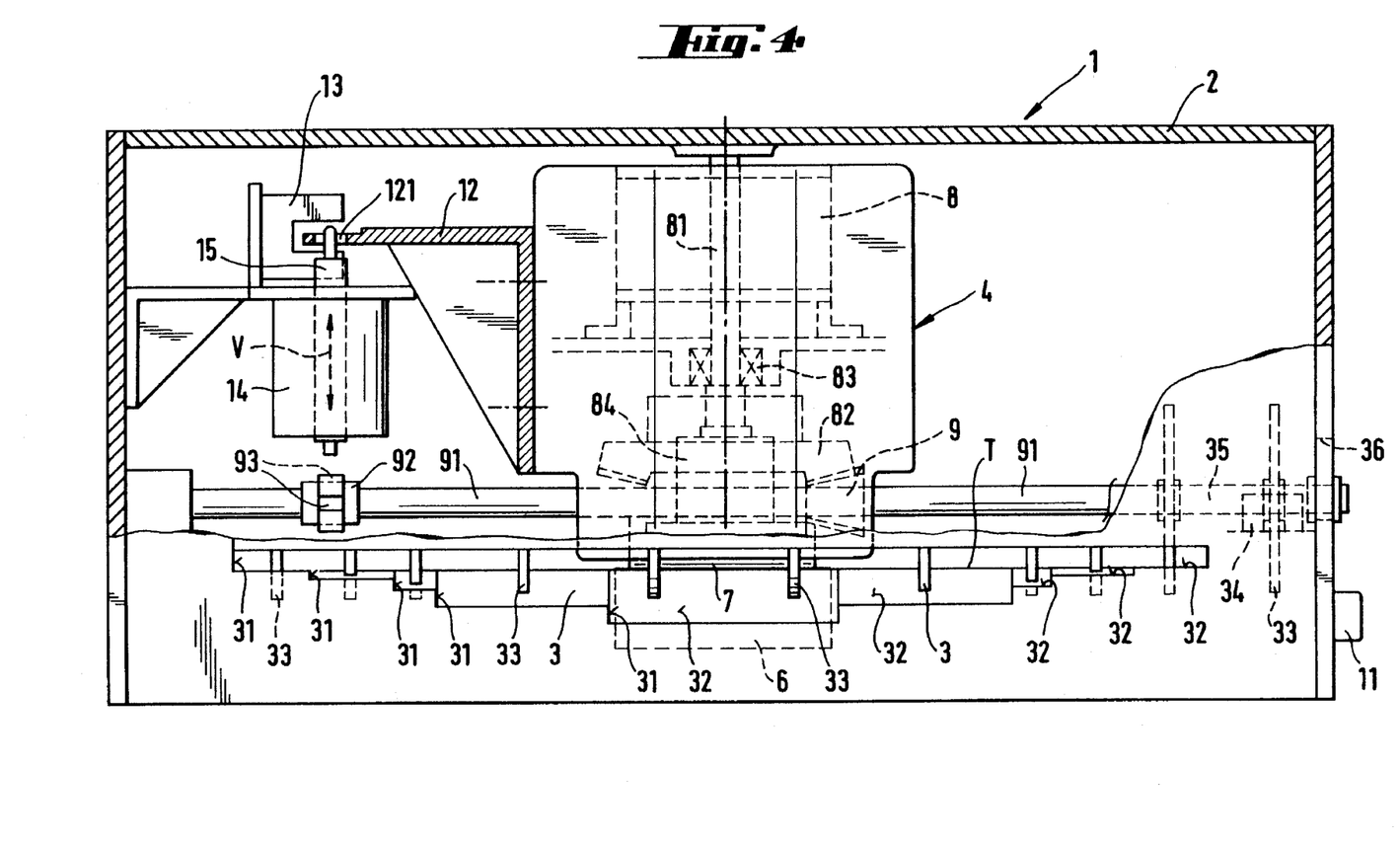
FIG. 4 shows a front view of the FIG. 1 apparatus in partial section.
Figure 6:
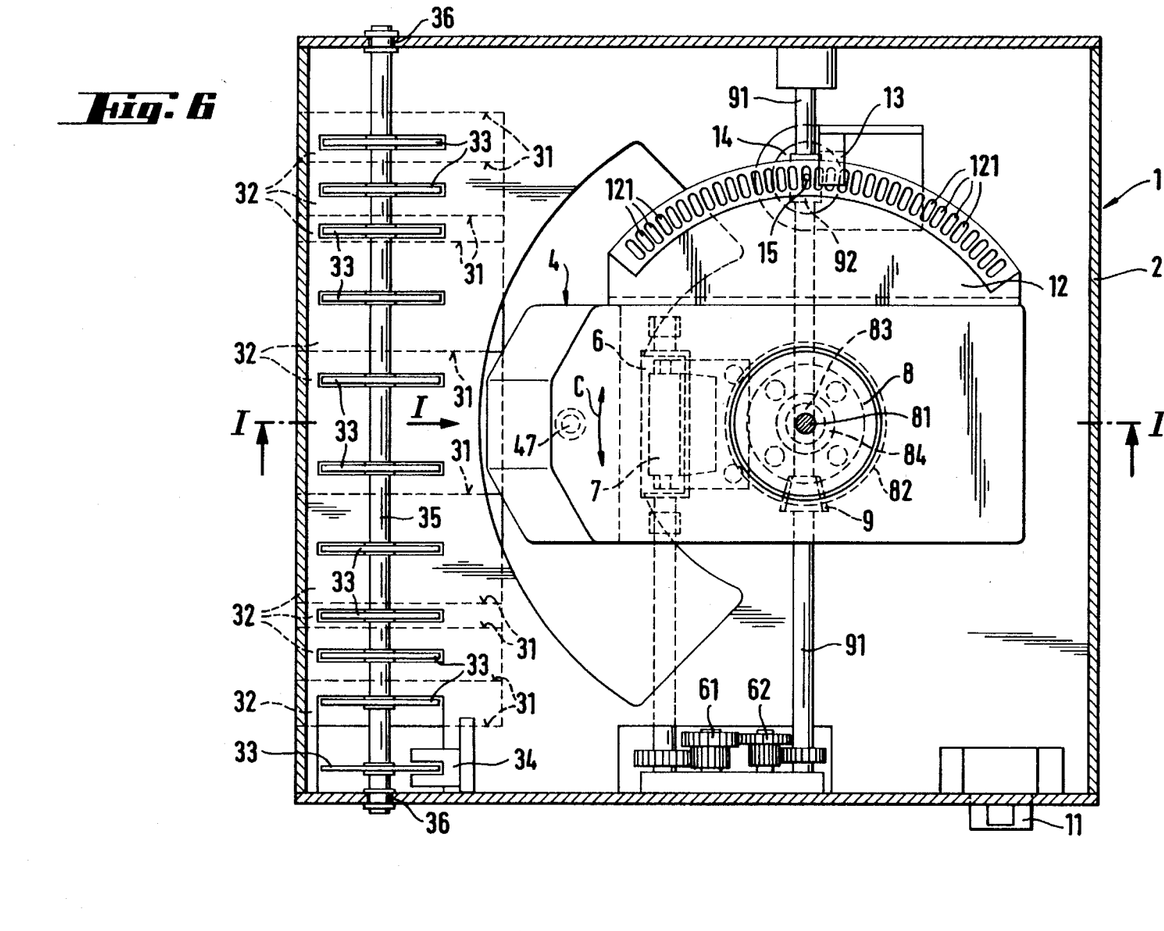
FIG. 6 shows a top view of the apparatus according to FIG. 1.

An exemplary embodiment of an apparatus according to the invention for recording photometric data that is positioned side by side or in succession on a page-like or strip-like print is illustrated in FIGS. 1, 4, and 6 by the reference numeral 1. In its design the apparatus reveals certain similarities with the apparatus described in U.S. Pat. No. 5,118,183. Specifically, it comprises a housing 2 with an intake slot 3. Provided in the area of the intake slot 3 on at least one side is at least one stop 31 for the print P. Positioned inside of the housing is a transport device 6, 7 for the automatic transport of a print P into the housing interior along a transport path T. A reflectance measuring unit 4 with a reflectance measuring lens 41 for opaque prints is positioned along the transport path T, along with a transmission measuring unit 5 with a transmission measuring lens 51 for transparent prints. During its transport over the transport path, the print P is moved past both measuring units. In the case of an opaque print, the print is measured by the reflectance measuring unit 4, and in the case of a transparent print, the print is measured by the transmission measuring unit 5.

While the depicted embodiment is an apparatus with a combined reflectance and transmission measuring unit, the apparatus according to the invention can also be outfitted with only a reflectance measuring unit. In this case, the apparatus is suitable only for the measurement of opaque prints.

Figure 2:
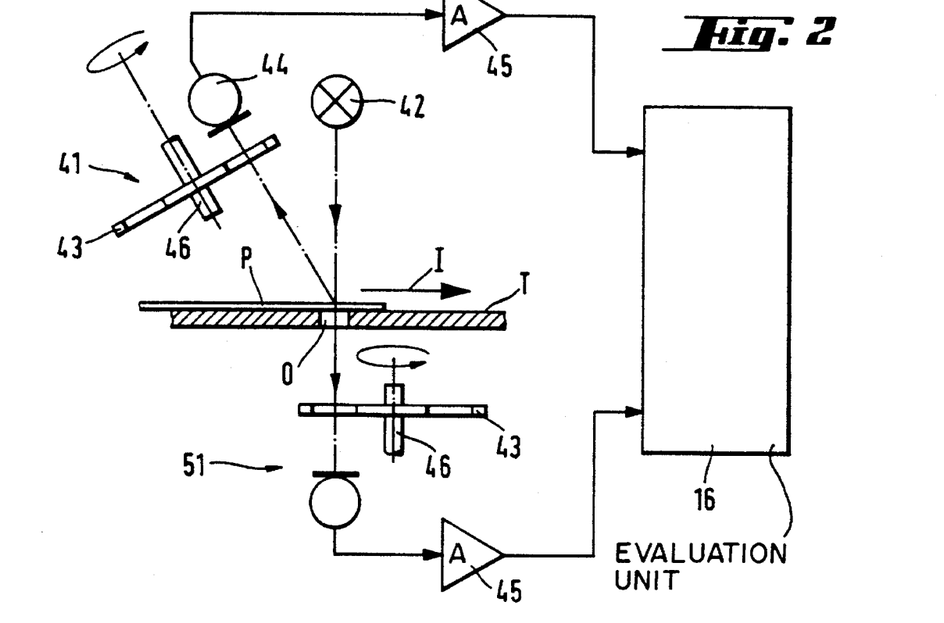
FIG. 2 shows an exemplary combined reflectance measuring unit and a transmission measuring unit within the FIG. 1 apparatus.

The basic construction of an exemplary combined reflectance and transmission measuring unit, as realized, e.g, in densitometers of the applicant, is illustrated in FIG. 2. The reflectance measuring unit includes, a reflectance measuring lens 4 1 comprising a light source 42, a wavelength dispersion unit 43, a photoelectric receiver 44 positioned behind the wavelength dispersion unit 43, and a signal amplifier 45. For ease of illustration, focusing lenses are not shown in FIG. 2. The reflectance measuring unit is positioned above the transport plane T in such a way that it can receive light reflected from an opaque print. The reflected light is collected and conducted through the wavelength dispersion unit 43 to the photoelectric receiver 44. The electrical signals produced by the photoelectric receiver are amplified and passed on to an evaluation unit 16, where the signals are convened and evaluated. The evaluation unit 16 is connected to input/output units (FIG. 3), by means of which information can be communicated (e.g, the type of print P relative to the evaluation unit, and by means of which the given photometric data can be displayed in an appropriate form. The input unit provided is conventionally a keyboard or field of keys. The output unit may be a picture screen (e.g., monitor) or a printer. The wavelength dispersion unit can advantageously take the form of a filter wheel 43 which rotates on an axis that is connected to a motor 8 (FIG. 1) by means of a toothed belt 48.

The exemplary transmission measuring unit 5 is positioned below the transport plane T for the print P. It comprises a transmission measuring lens 51, whose design can be very similar to that of the reflectance measuring lens 41. A basic difference is that the transmission measuring unit, unlike the reflectance measuring unit, does not have a separate light source, but rather uses the light source 42 of the reflectance measuring lens 41. Here the light from the light source 42 positioned above the transport plane T is conducted from the reflectance measuring lens 41 through a transparent print and through an opening O in the transport plane T to the transmission measuring lens 51; it is collected there, recorded, and converted into electrical signals which are passed on to the evaluation unit 16, where the signals are evaluated according to preselected spectral parameters.

Figure 3:
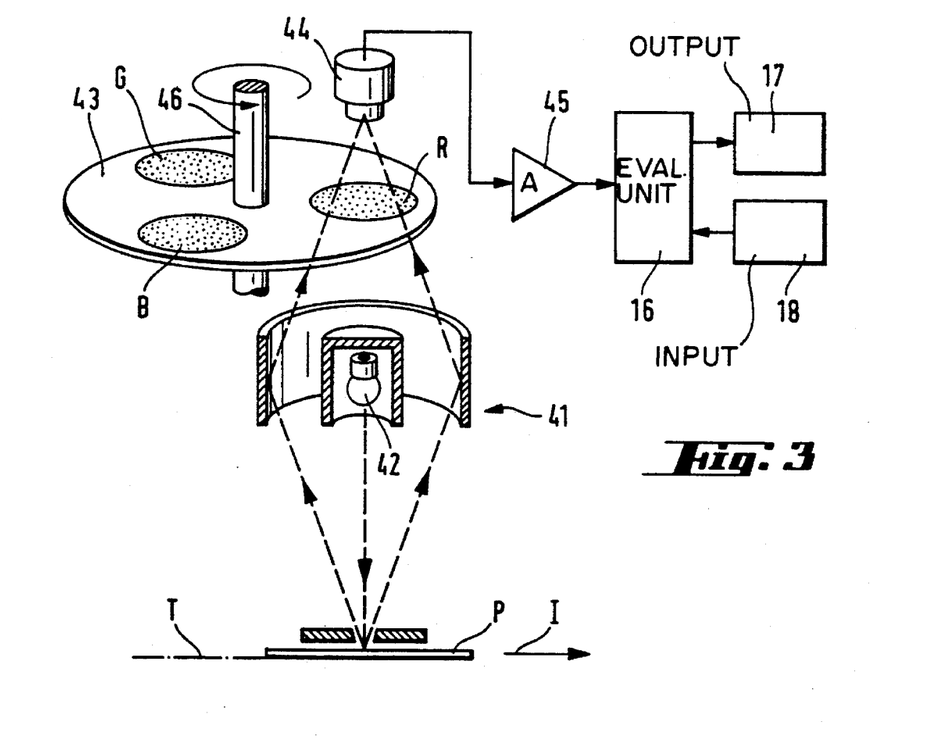
FIG. 3 shows a detailed illustration of the reflectance unit according to FIG. 2.

FIG. 3 shows a reflectance measuring unit in greater detail. Shown here is a measuring unit like that described in U.S. Pat. No. 4,645,350. From the schematic depiction it can be seen that the filter wheel 43 includes spectral filters which permit, for example, an analysis of a print P into the three primary colors of red R, green G, and blue B. By rotating the filter wheel 43 around axis 46, the different color filters are rotated into the light path of the measuring light source 42. Also shown in FIG. 3 are an output unit 17 for the photometric data established and an input unit 18 for transmitting input information to the evaluation unit 16.

In the exemplary embodiment of the invention shown in FIGS. 1 and 4–7, the evaluation unit 16 is a console positioned within the housing below the transport plane T; the console is equipped with circuits (e.g., integrated circuits and other electronic components).

The apparatus 1 shown in FIGS. 1, 4, and 6 can be designed to accommodate the passage of the prints P through the device. To this end, FIG. 1 includes an outlet slot 10 on a side of the housing 2 opposite the inlet slot 3; prints P are ejected from the device through this outlet slot 10. In an alternate variant of the FIG. 1 apparatus, the outlet slot can be designed for integration with other facilities, for example, a photographic printer. In this case, a print P would conventionally be ejected through the intake slot 3 after measurement of the measuring fields on the print. Here the transport device 6, 7 must naturally be able to operate in both directions.

An attachment jack 11 can also be provided, as shown in FIGS. 1 and 6. This attachment jack 11 is intended to receive a plug from a power source and to provide for the exchange of data. This permits the apparatus to be integrated into existing control systems. In this manner an external data terminal can communicate with the evaluation unit 16 provided in the apparatus.

Exemplary embodiments of an apparatus according to the invention differ from, for example, an apparatus described in U.S. Pat. No. 5,118,183 which reflects the state-of-the art. For example, the stop 31 (FIG. 5) for the print P is stationary relative to the intake slot 3, while at least the reflectance measuring lens 51 and the print P seized by the transport device 6, 7 can move relative to each other, in a direction transverse to the intake direction I (FIG. 5) of the print P. This permits adjacent measuring field columns to also be measured without having to reposition the print between the individual measurements. Limiting the capacity for movement to the reflectance measuring lens is due to the fact that it is generally only opaque prints, for example, paper test strips, that exhibit a number of adjacently positioned measuring field columns. With transparent prints—for example, film test strips—the measuring fields are typically positioned in a single column and, in addition, are symmetric to the central track of the print. Naturally the transmission measuring lens can also be given the capacity for movement relative to the print in order to permit transparent prints with adjacently positioned measuring field columns to be measured in an advantageous manner. But since such prints hardly exist, this variant of the apparatus will not be described in any greater detail. The following embodiments are therefore restricted to an apparatus in which only the reflectance measuring lens 51 and the print P seized by the transport device 6, 7 can be moved relative to each other in a direction transverse to the intake direction I (FIG. 5) of the print P.

In an advantageous variant of the invention, which is also relatively easy to realize, the reflectance measuring lens 41 can be moved out of an initial position in a transverse direction relative to the print P; for example, it can be swiveller on a swivel axis. Here a light inlet aperture 47 (FIGS. 1, 6) describes an arc which rests on a plane parallel to the transport path T. The light inlet aperture of the reflectance measuring lens 41 is usually located only a short distance above the transport plane T. The distance between the lower rim of the light inlet aperture 47 and the transport plane is given by the position of the aperture 47 in the reflectance measuring unit 4. Care can be taken to adjust the distance to as small a distance as possible, both to capture as much light reflected from the print as possible and to avoid the inlet of diffused light.

The initial position of the reflectance measuring lens 41 can be a position in which the light source 42 (FIG. 3) of the reflectance measuring lens is located precisely above the transmission measuring lens 51. Here an intensity measurement can be performed with the help of the transmission measuring lens 51 while the reflectance measuring lens 41 is being swivelled. The position of the reflectance measuring lens 41 in which the light source 42 is positioned precisely above the transmission measuring lens 51 and at which the transmission measuring lens measures the maximum intensity is defined as the initial position. When an apparatus 1 does not have a transmission measuring lens, the initial position of the reflectance measuring lens 41 can be located by maximum swivelling to extreme positions. The extreme positions are defined by stops on the right and left. The initial position of the reflectance measuring lens 41 can then be defined as the central position of the reflectance measuring lens 41 between the two extreme positions.

The swivel axis of the reflectance measuring lens 41 can advantageously be the drive axis 81 (FIG. 1) of the electromotor 8 for the filter wheel 43, both of which are positioned in the reflectance measuring lens. Here the rotating axis 46 of the filter wheel 43 is driven by a transmission belt 48 or by comparable power-transmission means. Thus, the reflectance measuring lens 41 can be swivelled by means of the drive motor 8 of the filter wheel 43. At its end facing the transport plane T the drive axis 81 of the electromotor 8 carries a bevel wheel-gearwheel, having teeth which engage the teeth of a second bevel wheel-gearwheel 9 which is rigidly positioned on a shaft 91 (FIG. 4). The drive axis 81 is also supported by a special bushing, which includes a lead-through, with mounting, for the drive shaft. In this manner, a support for both the drive axis 81 and the shaft 91 is provided, and unimpeded rotation of the shaft 91 and the drive axis 81 is assured. Intermediate gearwheels 61, 62 (FIG. 1) transmit drive force from the second bevel-gearwheel 9 to the transport device 6, 7, which in the present embodiment can be formed by a driven paper-drive roller 6 and a counterpressure roller 7. A print P, which is inserted through the intake slot, reaches the area between the two rollers 6, 7, is seized by them, and is transported onwards. Thus, the transport device 6, 7 for the print P is also coupled with the drive motor 8 for the filter wheel 43.

Relative to the intake direction I (FIG. 5) of the print P into the apparatus, the rollers 6, 7 (FIG. 1) of the transport device are positioned a short distance behind the reflectance measuring lens 51; for example, behind its intake aperture 47. This assures that the print is always held in position by the transport rollers 6, 7 when measuring fields located at the back terminal area of the print have to be measured. The distance of the transport rollers 6, 7 from the intake aperture 47 of the reflectance measuring lens 41 can vary in a range from about 15 mm to about 35 mm, or greater, and can preferably be about 25 mm. This assures that measuring fields in a front area of the print P can also be measured when the front end of the print P has been seized by the transport rollers 6, 7.

A further bearing 83 (FIG. 4) is provided on the drive axle 81 above the bushing 84 and permits unimpeded swivelling of the reflectance measuring lens 41, or in the depicted embodiment, of the entire reflectance measuring unit 4, around the drive axle 81. Swivelling the reflectance measuring lens 41, or the entire measuring unit 4, exploits the fact that with the rotation of the drive shaft 81 of the electromotor 8, the stator of the motor which is firmly connected to the measuring unit 4 by the motor housing, tends to rotate in an opposite direction due to the reception of angular momentum. Since the pivot bearing 83 permits the measuring unit 4 to turn around the drive axle 81, the measuring unit 4 has a tendency to swivel in a direction opposite the rotational direction of the drive shaft 81.

Figure 7:
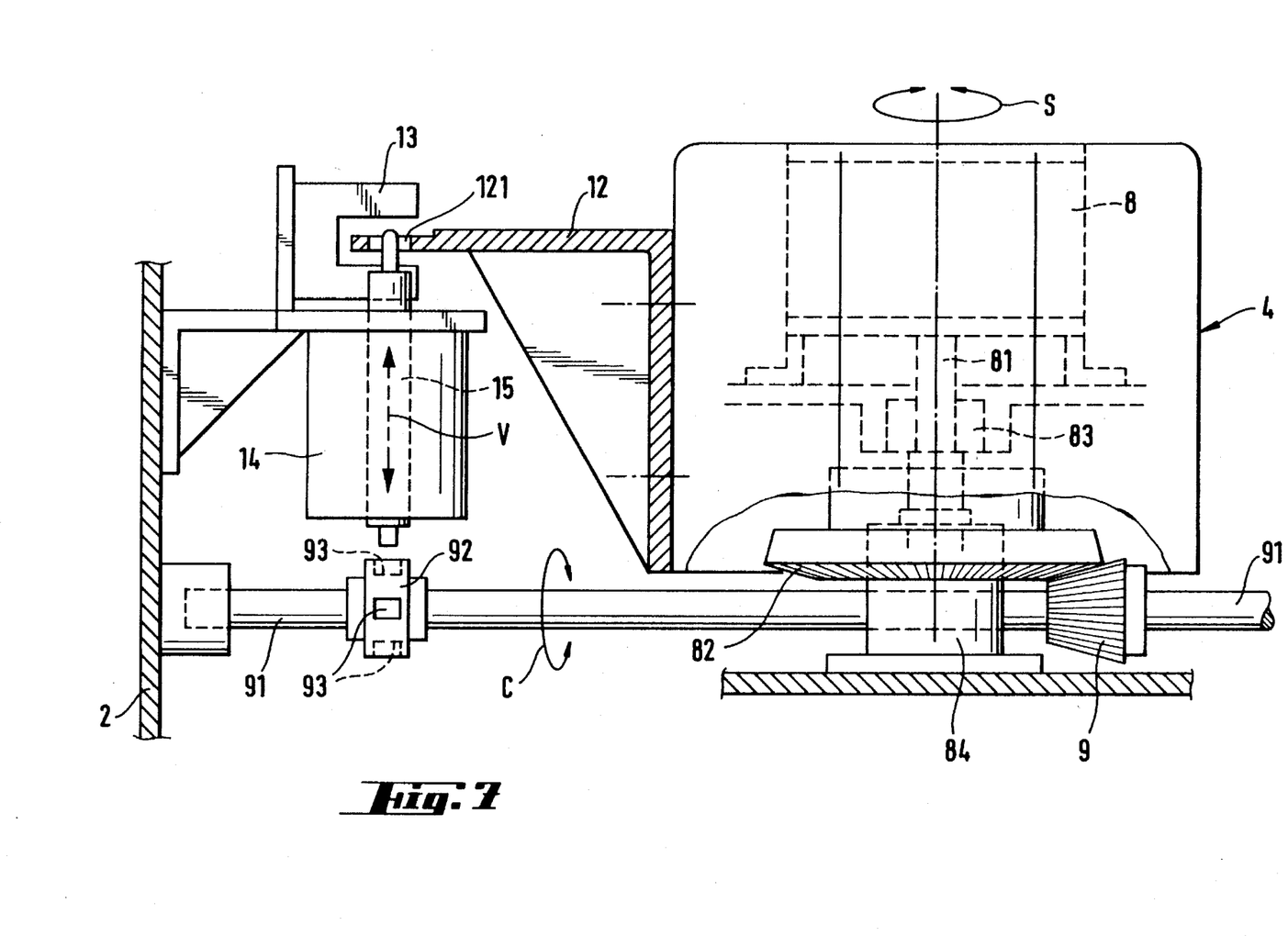
FIG. 7 shows a detailed view of a drive clutch between the reflectance measuring lens and the transport device.

Since the measuring unit's tendency to swivel is intrinsic to the design of the system, it must be assured that swivelling only occurs when intended and that when swivelling does occur it occurs in a controlled fashion. This means provisions must always be taken to control the degree of swivelling, i.e., the angle of swivelling. FIGS. 4, 6, and 7 schematically depict an exemplary embodiment of constructive measures intended to control the swivelling of the reflectance measuring unit 4. In FIG. 7 it can be seen that the reflectance measuring unit 4 is equipped with a device 12 which, in conjunction with locking elements 14, 15 (see FIG. 4), prevents unintended swivelling of the measuring unit 4. Specifically involved here is an arc-shaped guide piece 12 that is attached to the measuring unit 4. The guide piece 12 can be, e.g, a sheet of metal. The curvature of the guide piece and its position on the measuring unit 4 are selected in such a way that the drive axis 81 of the electromotor 8, which forms the rotational center of the measuring unit 4, is at the center of the arc that is established by the guide piece. The guide piece includes a series of somewhat elongated holes 121 (see FIG. 6), which are placed in screen-like fashion at uniform intervals. The holes are designed to engage with a catch 15, which can be brought in and out of position by actuating a lifting solenoid magnet 14 positioned beneath the guide piece 12. Thus, swivelling of the reflectance measuring unit 4 can be prevented in a simple fashion by moving the catch into a screen hole 121.

As depicted in FIG. 4, the swivel angle can be controlled by means of a light barrier fork 13 of conventional design. The light barrier fork 13 detects the number of screen holes 121 which have passed by it as the measuring unit 4 is swivelled out of its initial position. Since the screen holes are placed at uniform intervals, the angle of rotation can be deduced from the number of detected screen holes 121. In actual practice, a given swivel angle is established in the evaluation unit 16, as a preselected value, e.g., through the input unit. When the desired swivel angle is reached, the lifting magnet 14 is actuated and the catch 15 is driven into the screen hole 121 above it; thus the reflectance measuring unit is protected from further swivelling.

To safely move toward a desired position on the print P, it must also be guaranteed that the print P is at rest when the reflectance measuring lens 41, or the measuring unit 4, is being swivelled. Since the print P is seized by the transport device 6, 7, care must be taken to assure that the print is immobile during swivelling. To this end, a screen wheel 92 is positioned on the shaft 92 (FIGS. 4, 6), more or less below the lifting magnet 14, and is rigidly connected to the shaft 91. The screen wheel 92 includes a number of indentations 93 (FIG. 6) that are positioned at regular intervals over its face. The indentations 93 are positioned in such a way that, when the screen hole is released and the reflectance measuring unit is released for swivelling, the catch 15 of the lifting magnet 14 moves downwards into one of the indentations 93 of the screen wheel 92 and thereby arrests the shaft 91 and thus the transport device 6, 7 for the print P. The number of indentations 93 in the screen wheel 92 is optional; in an exemplary embodiment, four indentations 93 can be used.

The arc-shaped guide piece 12 provided with screen holes 121, the screen wheel 92 on the shaft 91 provided with indentations 93, and the lifting magnet 14 assure that either the reflectance measuring unit 4 or the transport device 6, 7, and with it, the print P, is always arrested. With the up and down movement of the catch 15 shown by the double arrow V in FIG. 7, either the reflectance measuring unit 4 is prevented from swivelling, as indicated by the double arrow S, or the shaft 91 is blocked against rotation (along with the transport device 6, 7), as indicated by the double arrow C in FIG. 7.

Figure 5:
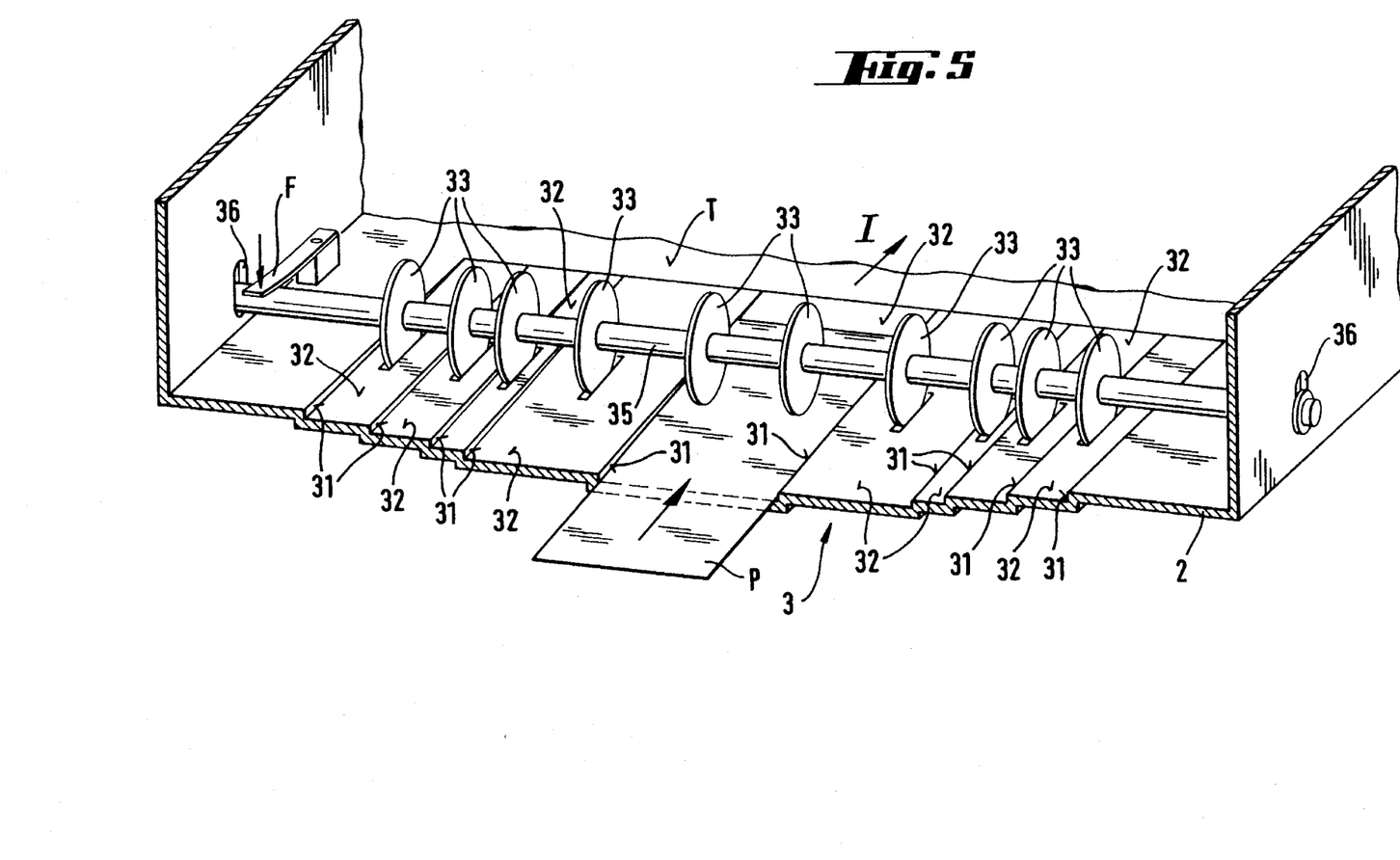
FIG. 5 shows a view of an intake area of the FIG. 1 apparatus in partial section.

The entrance side of the apparatus 1 according to the invention is shown in the left portion of FIGS. 1 and 6 and is separately depicted in FIGS. 4 and 5. The intake slot 3 has an approximately horizontal orientation. On at least one side of the intake slot at least one stop 31 is provided for the prints P. Several stops 31 are provided in the depicted embodiment for prints P of differing width; the stops are positioned on either side of the center of the intake slot 3. More specifically, five stops 31 are provided on each side, as shown in the exemplary embodiment of FIG. 4. The stops 31, counted outward from the center of the intake slot, are always identified with the same number and are designed to accommodate the width of the print P being guided in. The stops are preferably designed for prints P of 35 mm, 3.5 inches, 4 inches, 5 inches, and 6 inches width. Here the 35 mm format is typically used for transparent film test strips, while the other formats are typically used for the customary formats of photographic paper test strips. The positioning of the stops 31 is selected in such a way that the more inwardly located stops are intended for narrower prints P at a lower level than are the immediately adjacent stops. At each level a print guide element 32 leads in ramp-like fashion into the apparatus 1, beginning with the corresponding stops, until the level of the transport plane T is reached. While in the depicted embodiment stops 31 are provided for the longitudinal edges of the prints P on either side, the stops 31 naturally can be positioned on only one side of the intake slot 3.

Suppression rollers 33 (FIG. 5) or comparable moving means for holding the prints P in position are positioned directly behind the intake slot 3. The suppression rollers 3 can be positioned on a common axle 35 such that in each case at least two rollers rest against the corresponding ramp-like guide element 32 for the prints. The axle 35 is mounted on either side of the intake slot 3 in a vertical hole 36 of elongated shape and can be adjusted with respect to its height. Specifically, it can be moved from its resting position, and the suppression rollers along with it, against the force of gravity or the spring action of a suppressing spring F. In this manner a print P that is inserted into the intake slot 3 is squeezed between the given ramp 32 and the corresponding suppression rollers 33 and is thereby prevented from falling out. When the print P is advanced further into the apparatus 1, the suppression rollers rotate and hold the print P flat against the ramp-like print guide unit 32.

In an exemplary embodiment (FIGS. 1 and 6) the suppression rollers 33 are provided with elongated radial openings which interact with a light barrier fork 34. With the rotation of the suppression rollers 32 the light barrier is interrupted or released; the presence of a print P is detected in this manner. This information can then be used, e.g., to actuate the transport device 6, 7 of the apparatus 1 and the entire measuring unit 4, 5. Instead of the light barrier fork, a different sensor can be provided behind the intake slot—e.g., one which optically or mechanically detects the fact that a print P has been inserted.

A print P of a given standardized width, for example, an opaque test strip for examining the basic setting of the photographic printer, can be inserted into the horizontal intake slot 3 of the apparatus 1 according to the invention. The print, conventionally strip-like in form, is laid against the corresponding stops 31 and is guided at either longitudinal edge. The front end of the print P is pushed up the ramp-like print guide unit 32 into the intake gap 3. It is clamped between the suppression rollers 33 and the print guide unit 32. As the print P is further inserted, the suppression rollers 33 begin to turn. The rotation of the suppression rollers 33 is detected by the right barrier fork 34, and the apparatus 1 is actuated. This specifically affects the transport device 6, 7 for the print P and the measuring units 4, 5. The print P is manually inserted until it is seized by the transport rollers 6, 7. From this moment until the print is ejected the print is automatically transported by the apparatus 1.

The measurement of the measuring fields of the opaque print P is performed by the reflectance measuring unit 4. In the case of a transparent print P, e.g., a film test strip, the measurement is performed by the transmission measuring unit 5.

First the initial position of the swivelled reflectance measuring unit 4 is determined. In actual practice, this occurs before the print P is seized by the transport rollers 6, 7. The reflectance measuring unit is swivelled until the transmission measuring unit identifies the maximum light intensity. When this occurs, the light source 42 of the reflectance measuring lens 41 is positioned directly above the transmission measuring lens 51. The reflectance measuring unit 4 is then locked into this position. After the print P has been seized by the transport rollers 6, 7, the print P is measured at a predetermined longitudinal interval, for example, every 5 mm. The print P is analyzed into the three primary colors of red, green, and blue by means of the filters in the filter wheel. The measured reflectance values are transmitted to the electronic evaluation unit 16. In the electronic evaluation unit 16 the measured values are then compared with the predetermined data through cross-correlation. The predetermined data relate to the position of the measuring point on the standardized print and to the theoretical spectral data of the measuring point; they have already been fed into a storage unit of the electronic evaluation unit 16. The measured values are compared with the predetermined data until optimal agreement is reached. After evaluation of the first measuring field column—which is usually positioned in the approximate center of the strip-shaped print—the transport device is brought to a stop. Next the reflectance measuring unit 4 is swivelled according to the specifications of the standardized print until an adjacent measuring field column is positioned below the reflectance measuring lens 4. Evaluation of the measuring fields of the adjacent column is again performed in steps, preferably during transport of the print P in a direction opposite the intake direction. When this measurement is completed, the reflectance measuring unit can again be swivelled, to perform another measurement during its transport in the opposite direction, and so forth. The measured values are then evaluated in the electronic evaluation unit 16, and the desired spectral data are communicated to the user in the desired form, for example, via monitor or printer.

The apparatus and process according to the invention for recording photometric data that is positioned in succession or in adjacent fashion on a page-like or strip-like print considerably reduce the labor required to correctly position the test strip. The operator no longer has to decide whether, and to what degree, a test strip must inserted in a laterally displaced fashion. The apparatus allows adjacent measuring field columns to be evaluated without the need to reorient the test strip for each measuring field column. Adjacent measuring field columns can then be evaluated when the test strip has been seized by the transport device positioned in the apparatus. In addition, the apparatus can faultlessly evaluate test strips of differing width or length and with a varying placement of the measuring fields.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description and all changes which come within the meaning and range of equivalents thereof are intended to be embraced therein.

What is claimed is:

1. Apparatus for recording photometric data that is positioned in succession or in adjacent fashion on a page-like or strip-like print, comprising:

a housing with an intake slot having, on at least one side, at least one stop for a print, each stop being stationary relative to the intake slot;

a transport device positioned within an interior of the housing for automatic intake of the print along a transport path into the housing;

at least one measuring unit for measuring prints, said at least one measuring unit being positioned, relative to an intake direction of the print, in front of the transport device within the housing such that the measuring unit is passed by the print when said print is drawn into the housing interior, said at least one measuring unit being connected to an evaluation unit, at least a portion of said measuring unit being movable relative to the print in a direction transverse to the intake direction of the print; and a wavelength dispersion unit for measuring the print in different colors.

2. Apparatus according to claim 1, further including:

a transmission measuring unit and a reflectance measuring unit having a reflectance measuring lens, the reflectance measuring lens being positioned above the transport path of the print, while the transmission measuring unit and its transmission measuring lens are positioned below the transport path.

3. Apparatus according to claim 2, further including:

means for moving the reflectance measuring lens out of an initial position in a direction transverse to the intake direction of the print.

4. Apparatus according to claim 3, wherein the moving means can swivel the reflectance measuring lens to a position opposite its initial position such that a light intake aperture of the reflectance measuring lens describes an arc during swivelling which lies on a plane that is parallel to the transport path.

5. Apparatus according to claim 4, wherein the reflection measuring unit further includes:

a lamp positioned exactly above the transmission measuring lens of the transmission measuring unit when the reflectance measuring lens is in its initial position.

6. Apparatus according to claim 4, wherein the wavelength dispersion unit includes a filter wheel which is driven by a drive motor, and the reflectance measuring lens is swivelled by the moving means which includes the drive motor for the filter wheel.

7. Apparatus according to claim 6, wherein the transport device for the automatic intake of the print further includes:

at least one pair of rollers or cylinders which, relative to the intake direction, is positioned at a distance of about 15 mm to 35 mm behind the reflectance measuring lens and one of the rollers or cylinders is driven by the drive motor of the filter wheel.

8. Apparatus according to claim 7, further including:

a stopping device for stopping the reflectance measuring lens and the transport device such that either the reflectance measuring lens is kept from swivelling or the transport device is stopped.

9. Apparatus according to claim 1, wherein the intake slot is approximately horizontal and includes, on at least one side, plural stops for prints of different width, said stops being positioned such that a first stop for narrower prints is located closer to a center of the intake slot than an adjacent stop for prints of greater width, said first stop being positioned at a lower level than the adjacent stop for wider prints, said housing further including:

a guide unit for the prints which rises from the plural stops in ramp-like fashion up to a level of the transport path.

10. Apparatus according to claim 9, wherein the plural stops are provided on either side of the intake slot center such that longitudinal sides of each print rest against a stop.

11. Apparatus according to claim 1, further including:

movable suppression means to hold the prints in place, said movable suppression means being positioned immediately behind the intake slot and being movable against gravity or a spring bias out of their resting position on a print guide unit.

12. Apparatus according to claim 1, further including:

a sensor positioned behind the intake slot which detects presence of a print and actuates the apparatus in the presence of a print.

13. Apparatus according to claim 12, further including:

movable suppression means to hold the prints in place, said movable suppression means being positioned immediately behind the intake slot and being movable against gravity or a spring bias out of their resting position on a print guide unit, and said sensor being a rotating sensor which identifies rotation of a suppression roller of the movable suppression means.

14. Apparatus according to claim 1, wherein said apparatus is a "stand alone" device which includes:

an outlet slot for the prints which is positioned on a side of the apparatus opposite the intake slot.

15. Apparatus according to claim 1, wherein said transport device is a reversible device, such that after measuring fields of a print have been measured, the transport device can be operated in reverse direction such that the print is ejected from the intake slot.

16. A process for recording photometric data that is positioned in succession or in adjacent fashion on a page-like or strip-like print, comprising the steps of:

feeding a page-like or strip-like print with measuring fields that are positioned in succession or in adjacent fashion through an intake slot that includes, on at least one side, at least one stop for the prints wherein each stop is stationary relative to the intake slot;

automatically drawing, via a transport device positioned within a housing, the print along a transport path into the housing and conducting it past a measuring unit which is positioned relative to the intake direction of the print, in front of the transport device within the housing and which is connected to an evaluation unit;

measuring the prints by the measuring unit and analyzing the prints, in different colors by means of a wavelength dispersion unit;

transmitting recorded data to the evaluation unit for further processing; and moving at least a portion of the measuring unit and the print relative to each other in a direction transverse to the intake direction of the print and toward adjacently positioned measuring fields of the print.

17. A process according to claim 16, further including a step of:

measuring opaque prints using a reflectance measuring unit having a reflectance measuring lens;

measuring transparent prints by means of a transmission measuring unit with a transmission measuring lens; and analyzing measured prints in at least three different colors.

18. A process according to claim 17, further including a step of:

transversely moving the reflectance measuring lens from an initial position opposite the print.

19. A process according to claim 18, further including a step of:

determining the initial position of the reflectance measuring lens in the absence of the print using an intensity measurement performed by the transmission measurement unit while the reflectance measuring lens is being moved transversely, the position of the reflectance measuring lens at which a maximum intensity is measured by the transmission measuring unit being defined as the initial position.

20. A process according to claim 17, further including a step of:

driving a filter wheel of the wavelength dispersion unit by a drive motor.

21. A process according to claim 20, further including a step of:

driving the reflectance measuring lens and the transport means for the print by the drive motor of the filter wheel, with either the transport means for the print or the reflectance measuring lens alone being moved, so that the reflectance measuring lens is only moved transversely relative to the print when the print is at rest and vice versa.

22. A process according to claim 16, further including a step of:

feeding the prints in an approximate horizontal orientation to the intake slot which includes, on at least one side, plural stops for prints of different width, the stops being positioned such that a first stop for a narrower print is located closer to a center of the intake slot than an adjacent stop of greater width, and the first stop for a narrower print is positioned at a lower level than the adjacent stop for wider prints; and advancing the prints from said plural stops over a ramp-like guide unit up to a level of the transport path within the apparatus.

23. A process according to claim 22, wherein stops are provided on either side of the intake slot center, said process further including a step of:

guiding each print on either longitudinal side by a stop.

24. A process according to claim 16, further including a step of:

transporting the prints beneath a movable suppression means to hold the prints in place, said movable suppression means being positioned immediately behind the intake slot and moved against gravity or a spring bias out of their resting position against a print guide unit.

25. A process according to claim 16, further including steps of:

detecting the presence of a print using a sensor provided behind the intake slot; and actuating the apparatus in the presence of a print.

26. A process according to claim 25, further including steps of:

storing, for standardized prints, a position of a measuring point on the print and spectral data of the measuring point in a storage unit of the evaluation unit;

measuring the print over a predetermined longitudinal interval; and comparing the measured values with the data stored in the storage unit using cross-correlation until optimal agreement between the measured data and the stored data is achieved.

27. A process according to claim 26, further including a step of:

measuring the print column by column, and measuring an adjacent column by passing the print under the measuring unit in the opposite direction.

28. A process according to claim 16, further including a step of:

ejecting the print through an outlet gap located on a side of the apparatus opposite the intake slot after the measuring fields have been measured.

29. A process according to claim 16, further including a step of;

ejecting the print through the intake slot after the measuring fields have been measured.

30. Apparatus for processing printed data comprising:

a housing with an intake slot having at least one stop for a print, said at least one stop being stationary relative to the intake slot;

a transport device positioned within the housing for transporting the print along a transport path into the housing;

at least one measuring unit for measuring the print, said at least one measuring unit being positioned within the housing such that the measuring unit is passed by the print when said print is drawn into the housing, at least a portion of said measuring unit being movable relative to the print in a direction transverse to the intake direction of the print; and a wavelength dispersion unit for measuring a plural color components of the print.

31. Apparatus according to claim 30, further including:

a transmission measuring unit having a transmission measuring lens, and a reflectance measuring unit having a reflectance measuring lens being positioned on a first side of the transport path of the print, while the transmission measuring lens is positioned on a second side of the transport path opposite said first side.

32. Apparatus according to claim 31, further including:

means for swivelling the reflectance measuring lens to a position opposite an initial position such that a light intake aperture of the reflectance measuring lens describes an arc during swivelling which lies on a plane that is parallel to the transport path.

33. Apparatus according to claim 32, wherein the transport device automatically intakes the print and further includes:

at least one pair of rollers or cylinders which, relative to the intake direction, is positioned at a distance of about 15 mm to 35 mm behind the reflectance measuring lens; and a drive motor for driving a filter wheel of the wavelength dispersion unit and for driving one of the rollers or cylinders.

34. Apparatus according to claim 33, further including:

a stopping device for stopping the reflectance measuring lens and the transport device such that the reflectance measuring lens is kept from swivelling when the transport device is moving, and the transport device is stopped when the reflectance measuring lens is swivelling.

35. Apparatus according to claim 34, further including:

movable suppression means to hold the print in place, said movable suppression means being positioned immediately behind the intake slot and being movable against gravity or a spring bias out of a resting position on a print guide unit; and a rotating sensor which identifies rotation of a suppression roller of the movable suppression means to activate the apparatus.

36. Apparatus according to claim 35, wherein the intake slot is approximately horizontal and includes, on at least one side, plural stops for prints of different width, said stops being positioned such that a first stop for narrower prints is located closer to a center of the intake slot than an adjacent stop of greater width, said first stop being positioned at a lower level than the adjacent stop for wider prints, said housing further including:

a guide unit for the prints which rises from the plural stops in ramp-like fashion up to a level of the transport path.

* * * * *